United States Patent
Niekawa et al.

(10) Patent No.: US 8,193,509 B2
(45) Date of Patent: Jun. 5, 2012

(54) RADIATION IMAGE DETECTOR

(75) Inventors: Yukihiro Niekawa, Hachioji (JP); Yoshihiko Eguchi, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 0 days.

(21) Appl. No.: 13/060,160

(22) PCT Filed: Feb. 27, 2009

(86) PCT No.: PCT/JP2009/053641
§ 371 (c)(1),
(2), (4) Date: Feb. 20, 2011

(87) PCT Pub. No.: WO2010/021165
PCT Pub. Date: Feb. 25, 2010

(65) Prior Publication Data
US 2011/0147601 A1    Jun. 23, 2011

(30) Foreign Application Priority Data
Aug. 22, 2008 (JP) .................................. 2008-213703

(51) Int. Cl.
*H01L 27/146* (2006.01)
(52) U.S. Cl. .................................................. 250/370.09
(58) Field of Classification Search ....... 250/370.01–370.15; 378/98.8
See application file for complete search history.

(56) References Cited

U.S. PATENT DOCUMENTS

| | | | |
|---|---|---|---|
| 5,452,338 A | 9/1995 | Granfors et al. | |
| 5,773,832 A * | 6/1998 | Sayed et al. | 250/370.09 |
| 6,222,901 B1 | 4/2001 | Meulenbrugge et al. | |
| 6,977,988 B2 * | 12/2005 | Niwa | 378/95 |
| 7,041,955 B2 | 5/2006 | Andre et al. | |
| 7,460,641 B2 * | 12/2008 | Niwa | 378/95 |
| 7,563,026 B2 * | 7/2009 | Mandelkern et al. | 378/191 |
| 2004/0114725 A1 * | 6/2004 | Yamamoto | 378/189 |

FOREIGN PATENT DOCUMENTS

| | | |
|---|---|---|
| JP | 2000-347330 A | 12/2000 |
| JP | 2003-172783 A | 6/2003 |
| JP | 2003-210444 A | 7/2003 |
| JP | 2006-208305 A | 8/2006 |
| JP | 2008-134057 A | 6/2008 |

OTHER PUBLICATIONS

International Search Report for International Application No. PCT/JP2009/053641 mailed Apr. 7, 2009 with English translation.

* cited by examiner

*Primary Examiner* — Kiho Kim
(74) *Attorney, Agent, or Firm* — Cantor Colburn LLP (57) ABSTRACT

A radiation image detector including: an internal power supply section, which is capable of being charged, to supply power to each section; an external power supply terminal to receive power from an external power source to allow the internal power supply section to be charged; and a power supply control section to control supply of the power to the internal power supply section, the power being received from the external power source via the external power supply terminal, wherein when detecting that the external power supply terminal receives power from the external power source, the power supply control section judges an operating state of each section, and controls supply of the power to the internal power supply section according to the operating state of each section, the power being received from the external power source via the external power supply terminal.

9 Claims, 5 Drawing Sheets

RADIATION IMAGE DETECTOR

This is a U.S. national stage application of International Application No. PCT/JP2009/053641, filed on 27 Feb. 2009. Priority under 35 U.S.C. §119(a) and 35 U.S.C. §365(b) is claimed from Japanese Application No. JP2008-213703, filed 22 Aug. 2008, the disclosure of which is also incorporated herein by reference.

FIELD OF THE INVENTION

The present invention relates to a radiation image detector.

BACKGROUND OF THE ART

Currently, there is known a radiation image detector, which is a so-called flat panel detector (FPD), as a device to obtain radiation images for medical purposes, the radiation image detector in which solid state image sensors are two-dimensionally arranged. As such a radiation image detector, there are known a radiation image detector using a direct method by which radiation energy is directly converted into an electric charge by using photo conductive material such as a-Se (amorphous selenium) as radiation detection elements, and the electric charge is read as electric signals of their respective pixels by using switching elements for reading signals such as TFTs (Thin Film Transistors) being two-dimensionally arranged, and a radiation image detector using an indirect method by which radiation energy is converted into light by using scintillators or the like, and the light is converted into an electric charge by using photoelectric conversion elements such as photo diodes being two-dimensionally arranged, and then the electric charge is read as electric signals by TFTs or the like.

No matter which method is used for a radiation image detector, it is known that radiographed image data needs to be corrected by gain correction, offset correction, and/or the like, the radiographed image data which is obtained by detecting a radiation by the radiation image detector, the radiation passing through a subject.

Gain correction values and offset correction values are necessary to perform the gain correction and the offset correction, respectively. Since these correction values fluctuate over time, the correction values are updated by regularly performing calibration on a radiation image detector, in general.

In particular, it is known that the fluctuation cycle of offset correction values is shorter than the fluctuation cycle of gain correction values (namely, offset correction value easily fluctuate), and that offset correction values largely change according to a temperature change and the like.

Hence, in order to understand the change of the characteristics of offset correction values over time, offset calibration which appropriately updates offset correction values is performed, the offset correction values calculated based on dark reading values which are obtained by regularly performing so-called dark reading by which electric signals are read without irradiating a radiation image detector.

When dark reading values are obtained, various electric noise, namely, dark current noise of a photo diode, TFT transient noise, TFT thermal noise, TFT leak noise, thermal noise caused by a parasitic capacitance of a data line which reads an electric charge from a TFT, amplifier noise inside a reading circuit, quantization noise caused by A/D conversion, and the like, are superposed on signals thereof, and influences the dark reading values, accordingly.

Therefore, when offset correction values are calculated, in many cases, in order to reduce the influence of the noise which is electrically superposed on signals read by the dark reading, the dark reading is performed on each of radiation detection elements multiple times. Then, the average value of dark reading values obtained thereby is obtained with regard to each of the respective radiation detection elements so that the obtained average values are used as the offset correction values. (Refer to Patent Documents 1 to 3, for example.)

Currently, there is developed a portable radiation image detector which has a built-in battery as an internal power supply section so as to be driven without a cable.

In addition, there are proposed a portable (cassette type) radiation image detector which has a built-in battery so as to be capable of radiography with a high degree of freedom by not using a cable, such as portable radiography at a bedside and the like, and also be capable of keeping radiography with no worries about the remaining charged amount of a battery by using a cable in a radiography room and the like so that power is supplied from an external power source (Patent Document 4, for example), and a portable radiation image detector to which power is supplied from a built-in battery when the portable radiation image detector is used by itself, and to which power is supplied from a Bucky device when the portable radiation image detector is loaded into the Bucky device (Patent Document 5, for example).

When a battery is charged by supplying power from an external power source, the battery is generally charged at a high speed by a large amount of power being supplied at a time from the external power source, and hence, a charging time of the battery is shortened.

Patent Document 1: U.S. Pat. No. 5,452,338
Patent Document 2: U.S. Pat. No. 6,222,901
Patent Document 3: U.S. Pat. No. 7,041,955
Patent Document 4: Japanese Patent Application Laid-open Publication No. 2003-172783
Patent Document 5: Japanese Patent Application Laid-open Publication No. 2000-347330

SUMMARY OF THE INVENTION

The Problems to be Solved by the Invention

However, when a large amount of power is supplied from an external power source in order to charge a battery while signals are read in order to obtain radiographed image data and/or dark reading values, noise is superposed on the signals, and a great influence is exerted on the radiographed image data and the dark reading values, accordingly.

When noise is superposed on signals, high-quality radiographed image data cannot be obtained. Moreover, when offset correction values are calculated by using dark reading values obtained from the signals on which noise is superposed, the accuracy of the offset correction values decreases.

Furthermore, in a radiation image detector used without a cable, obtained radiographed image data and dark reading values (or offset correction values calculated based thereon) are transmitted to an external device such as a console by wireless. When a large amount of power is supplied from an external power source in order to charge a battery while the obtained radiographed image data and dark reading values are transmitted, noise is superposed on signals thereof being in transmission, and influences the radiographed image data and dark reading values, accordingly.

The present invention is made in view of the circumstances. An object of the present invention is to provide a radiation image detector including an internal power supply section which can be charged, wherein signals of radiographed image data and the like can be prevented from being influenced by noise even when the internal power supply section is charged by power supplied from an external power source.

Means for Solving the Problems

To solve the problems mentioned above, the present invention is a radiation image detector including: an image data generation section including, a detection section in which a plurality of radiation detection elements are two-dimensionally arranged so as to be capable of extracting an electric signal of each pixel, a reading section to read the electric signal obtained by the detection section, and an arithmetic section; a communication section to transmit image data generated by the image data generation section to an outside of the radiation image detector; an internal power supply section, which is capable of being charged, to supply power to each of the sections including the detection section and the reading section; an external power supply terminal to receive power from an external power source so as to allow the internal power supply section to be charged; and a power supply control section to control supply of the power to the internal power supply section, the power being received from the external power source via the external power supply terminal, wherein when the power supply control section detects that the external power supply terminal receives power from the external power source, the power supply control section judges an operating state of each of the sections, and controls supply of the power to the internal power supply section according to the operating state of each of the sections, the power being received from the external power source via the external power supply terminal.

Advantageous Effects of the Invention

According to the present invention, when the external power supply terminal receives power from the external power source, the power supply control section judges an operating condition of each of the sections, and controls supply of the power, which is received from the external power source, to the internal power supply section according to the operating state of each of the sections.

Consequently, for example, in a case where a large amount of power is supplied from the external power source while a section which is easily influenced by noise is in operation, power supply from the external power source to the internal power supply section can be stopped, and the like. As a result, an effect can be obtained, the effect of preventing signals of radiographed image data and the like from being influenced by noise.

BEST MODE FOR CARRYING OUT THE INVENTION

In the following, a radiation image detector according to a preferred embodiment of the present invention is described referring to FIGS. 1 to 5. However, embodiments to which the present invention is applicable are not limited to the drawings.

Figure 1:
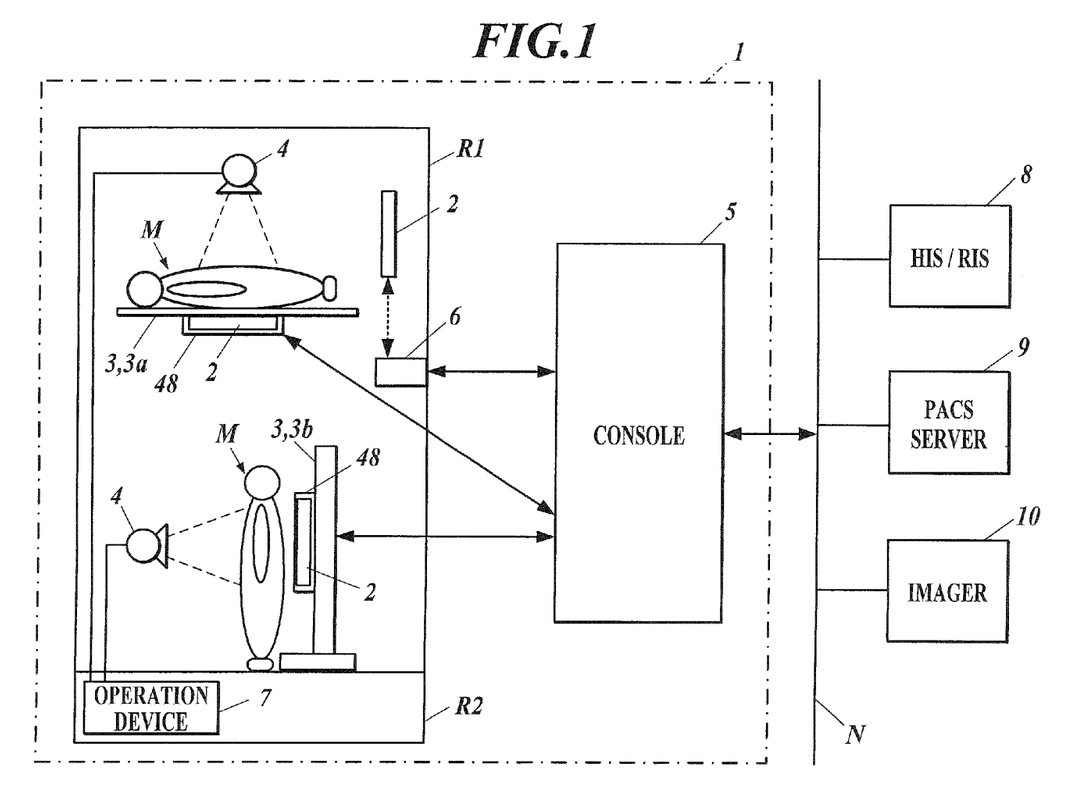
FIG. 1 is a schematic view showing a system structure of a radiography system according to an embodiment of the present invention.

A radiation image detector is placed, for example, in a radiography system 1 as shown in FIG. 1, and obtains radiation image data (hereinafter simply referred to as "image data").

The radiation image detector in the embodiment of the present invention is a cassette type FPD 2 (hereinafter referred to as a FPD cassette 2) which is a so-called flat panel detector (FPD) structured to be a cassette type (portable).

The radiography system 1 in the embodiment of the present invention includes the FPD cassette 2 and a console 5 which can communicate with the FPD cassette 2.

As shown in FIG. 1, the FPD cassette 2 is provided, for example, in a radiography room R1 where a subject (a region to be radiographed of a patient) which is a region (not shown) of a patient is radiographed by irradiation, and the console 5 is provided for the radiography room R1.

In the embodiment of the present invention, there is one radiography room R1 in the radiography system, and three FPD cassettes 2 are disposed in the radiography room R1, which is a case to be described as an example. However, the number of radiography rooms and the number of FPD cassettes 2 in the respective radiography rooms are not limited to the drawings.

Furthermore, when there is a plurality of radiography rooms R1, the console 5 is not necessarily provided for each of the radiography rooms R1. One console 5 may be provided for the plurality of radiography rooms R1.

Bucky devices 3 and radiation generators 4 are provided in the radiography room R1. Each of the Bucky devices 3 includes a cassette holding section 48 into which the FPD cassette 2 can be loaded and which can hold the FPD cassette 2, and each of the radiation generators 4 includes a radiation source such as an X-ray tube which irradiates a subject (a region to be radiographed of a patient M). The cassette holding section 48 is a section into which the FPD cassette 2 is loaded at the time of radiography. The cassette holding section 48 is not limited to being provided with the Bucky device 3. For example, the cassette holding section 48 may be provided with, for example, a cradle (not shown) including a terminal section through which a battery 28 described below can be charged and/or communications can be established using a wire.

FIG. 1 shows a case where one Bucky device 3a for radiography in the decubitus position and one Bucky device 3b for radiography in the standing position are provided in the radiography room R1. However, the number of Bucky devices 3 in the radiography room R1 is not limited thereto. Furthermore, in the embodiment of the present invention, the radiation generators 4 are provided with the Bucky devices 3, respectively. However, for example, one radiation generator 4 may be provided for a plurality of Bucky devices 3 in the radiography room R1, and be used by appropriately changing the position of the radiation generator 4, by changing the direction of irradiation thereof, and the like.

The radiography room R1 is a room which blocks radiations, and radio waves for wireless communications are blocked, accordingly. Therefore, a wireless access point (base station) 6 or the like is provided in the radiography room R1, the wireless access point through which communications between the FPD cassette 2 and an external device such as the console 5 are performed when the FPD cassette 2 and the external device such as the console 5 communicate with each other.

In addition, a preparation room R2 is provided next to the radiography room R1 in the embodiment of the present invention. In the preparation room R2, an operation device 7 is placed, the operation device 7 by which a radiologist, a doctor, or the like (hereinafter referred to as "operator") controls a tube voltage, a tube current, an irradiation-field diaphragm, and the like of the radiation generator 4 which irradiates a subject, and operates the Bucky device 3, and the like.

A control signal for controlling an irradiation condition of the radiation generator 4 is transmitted from the console 5 to the operation device 7. The irradiation condition for the radiation generator 4 is set according to the control signal transmitted from the console 5 to the operation device 7. The irradiation condition includes a start/end timing of irradiation, a value of the radiation tube current, a value of the radiation tube voltage, and a filter type.

An irradiation instruction signal which instructs irradiation is transmitted from the operation device 7 to the radiation generator 4. The radiation generator 4 delivers a prescribed radiation at a prescribed timing for a prescribed duration in accordance with the irradiation instruction signal.

In the embodiment of the present invention, as described below, the radiation generator 4 and the FPD cassette 2 are controlled to collaborate with each other such that the dark reading is performed at the FPD cassette 2 between the time when the irradiation instruction signal is transmitted and the time when irradiation actually starts. The radiation generator 4 performs irradiation after the irradiation instruction signal is received thereby and a necessary time for the dark reading elapses.

How much time after an irradiation instruction signal being transmitted, irradiation is actually performed; and how much time irradiation is performed; and the like are predetermined according to a region to be radiographed and the like. The radiation generator 4 performs irradiation based thereon.

An irradiation instruction signal may be transmitted to the radiation generator 4 after the dark reading ends.

Figure 2:
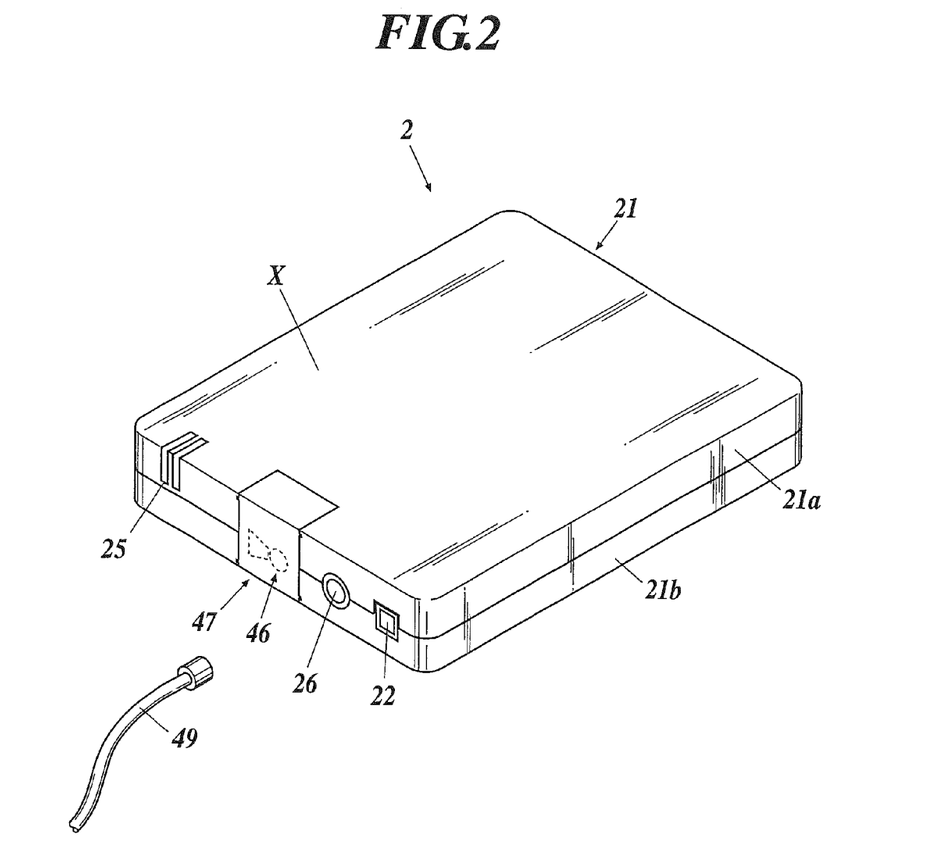
FIG. 2 is a perspective view showing a FPD cassette according to the embodiment of the present invention.

FIG. 2 is a perspective view showing the FPD cassette 2 according to the embodiment of the present invention.

As shown in FIG. 2, the FPD cassette 2 includes a case 21 which protects the inside of the FPD cassette 2. FIG. 2 shows the FPD cassettes 2 whose case 21 is composed of a front part 21a and a back part 21b. However, the shape and the structure of the case 21 are not limited thereto. The case 21 may be a tube-shaped case having a monocoque structure.

It is preferable that the size and the thickness of the FPD cassette 2 be the same as the size and the thickness of a CR cassette (not shown) so that the FPD cassette 2 can be used by being loaded into any of various Bucky devices 3 and the like which is set up for a CR cassette. More specifically, it is preferable, like a cassette CR, that the dimensions of the FPD cassette 2 comply with a standard for conventional screen/film cassettes, JIS Z 4905 (equivalent to an international standard, IEC 60406). In this case, the thickness of the FPD cassette 2 in the direction of irradiation is made between 15 mm-2 mm and 15 mm+1 mm. By being interchangeable with a CR cassette, existing equipment can be used as it is for radiography using the FPD cassette 2, which is convenient. The thickness of the FPD cassette 2 is not limited to the thickness mentioned above.

The FPD cassettes 2 having the size of 8 in.×10 in., 10 in.×12 in., 11 in.×14 in., 14 in.×14 in., 14 in.×17 in., 17 in.×17 in., and the like are prepared. However, the size thereof is not limited thereto.

As shown in FIG. 2, in the embodiment of the present invention, a power source switch 22, an indicator 25, a connector section 26, and the like are disposed on a lateral face of the FPD cassette 2.

The power source switch 22 is for switching ON and OFF of a power source of the FPD cassette 2. By operating the power source switch 22, a signal which instructs start and stop of power supply from the battery 28 (shown in FIG. 4) described below to each section of the FPD cassette 2 is output to a cassette control section 30 (shown in FIGS. 3 and 4). When the FPD cassette 2 is not used for radiography, the power source thereof is turned to OFF (namely, power supply from the battery 28 to each section of the FPD cassette 2 stops) so that consumption of the battery 28 can be held down.

The indicator 25 is composed of, for example, a LED and the like, and displays the remaining charged amount of the battery 28, operating states of various operations, and the like.

The indicator 25 notifies, for example, that the FPD cassette 2 is generating radiographed image data, performing the dark reading, transmitting image data to an external device, or the like, by blinks. The indicator 25 may notify by blinks that charging becomes available by connecting a cable 49 or the like to the connector section 26.

Figure 4:
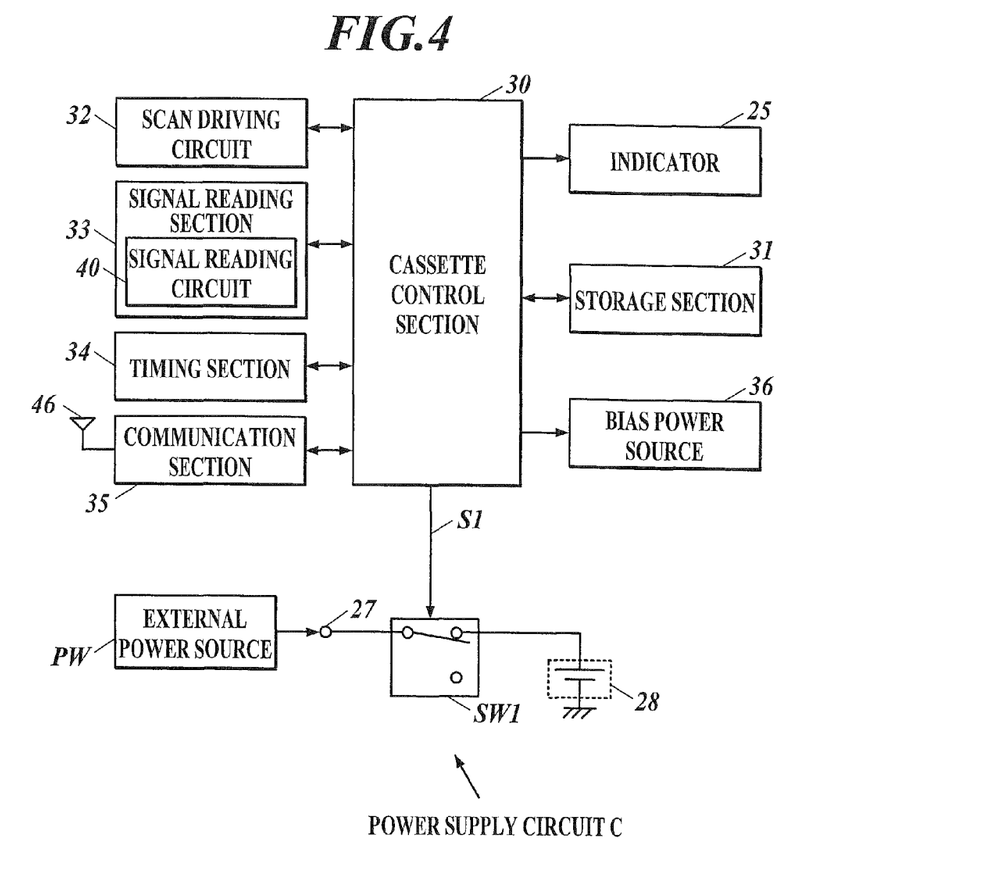
FIG. 4 is a main-part block diagram showing a functional structure of the FPD cassette shown in FIG. 2 and a power supply circuit which charges a battery.

The connector section 26 can be connected to the cable 49 which is connected to an external power source PW (shown in FIG. 4). An external power supply terminal 27 (shown in FIG. 4) to receive power from the external power source PW for supplying the power to the battery 28 is connected to the connector section 26. The battery 28 can be charged by connecting the cable 49 to the connector section 26.

Power may be directly supplied from the external power source PW to each section of the FPD cassette 2 by connecting the cable 49 to the external power supply terminal 27 via the connector section 26.

On a lateral face of the FPD cassette 2, a lid part 47 is provided, the lid part 47 which opens and closes for changing the battery 28 built in the case 21. An antenna device 46 is embedded in a lateral face of the lid part 47, the antenna device 46 for the FPD cassette 2 to transmit and receive information to/from an external device via the wireless access point 6 by a wireless method.

A scintillator layer (not shown) composed of scintillators which convert a delivered radiation into light is formed inside a radiation incident plane X (shown in FIG. 2) of the case 21. For the scintillator layer, a layer formed by using a phosphor in which luminescence center material is activated in parent material such as CsI:Tl, $Gd_2O_2S$:Tb, or ZnS:Ag can be used, for example.

On a face of the scintillator layer, the face which is opposite to a face on which a radiation is incident, a sensor panel section 24 as a detection section is provided, the sensor panel section 24 in which a plurality of photoelectric conversion elements 23 (shown in FIG. 3) to convert light outputted from the scintillator layer into electric signals are two-dimensionally arranged. The photoelectric conversion elements 23 are, for example, photo diodes, and form radiation detection elements with the scintillators, the radiation detection elements which convert a radiation passing through a subject into electric signals. The components of the radiation detection elements are not limited to the photoelectric conversion elements and the scintillators.

In the embodiment of the present invention, a reading section 45 (shown in FIG. 3) which is a reading section to read an output value of each of the photoelectric conversion elements 23 of the sensor panel section 24 includes the cassette control section 30, a scan driving circuit 32, and a signal reading section 33.

Figure 3:
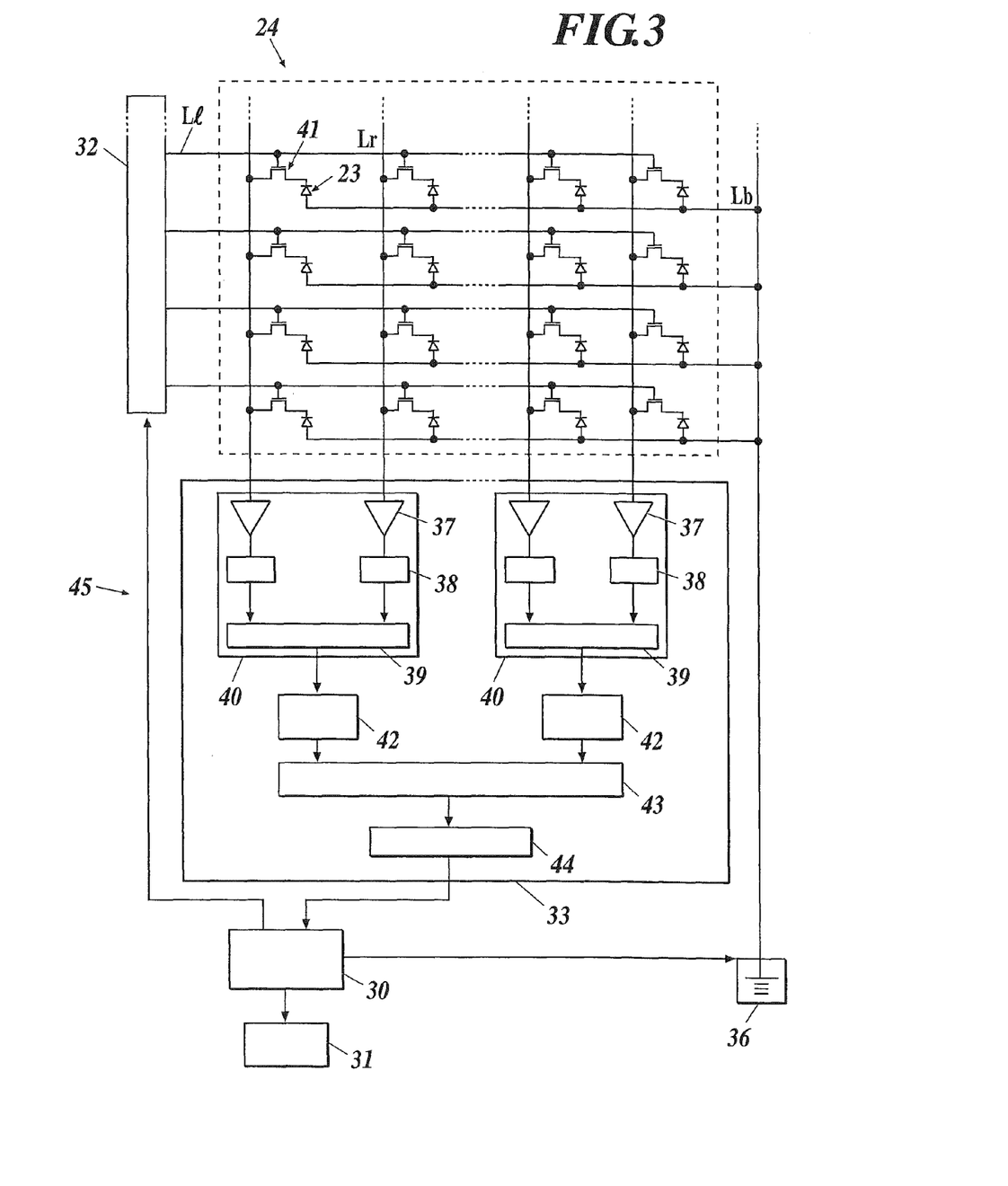
FIG. 3 is an equivalent circuit diagram showing a structure of a sensor panel section, a reading section, and the like of the FPD cassette shown in FIG. 2.

The structures of the sensor panel section 24 and the reading section 45 are further described referring to the equivalent circuit diagram of FIG. 3.

As shown in FIG. 3, with regard to each of the photoelectric conversion elements 23 of the sensor panel section 24, one electrode of the photoelectric conversion element 23 is connected to the source electrode of a TFT 41 which is a switching element for reading signals. The other electrode of the photoelectric conversion element 23 is connected to a bias line Lb. The bias line Lb is connected to a bias power source 36. Consequently, a bias voltage is applied to each of the photoelectric conversion elements 23 from the bias power source 36.

With regard to each of the TFTs 41, the gate electrode of the TFT 41 is connected to a scan line Ll which is extended from the scan driving circuit 32. The drain electrode of the TFT 41 is connected to a signal line Lr. The signal line Lr is connected to an amplifier circuit 37 in a signal reading circuit 40. An output line of the amplifier circuit 37 is connected to an analog multiplexer 39 via a sample-and-hold circuit 38. An A/D convertor 42 is connected to the analog multiplexer 39. A signal is converted from an analog signal into a digital signal by the A/D convertor 42. The converted signal is stored in an image data memory 43. The image data memory 43 is connected to the cassette control section 30 via a transmission circuit 44. In the embodiment of the present invention, the signal reading section 33 includes: the signal reading circuit 40 including the amplifier circuit 37, the sample-and-hold circuit 38, and the analog multiplexer 39; the A/D converter 42; the image data memory 43; and the transmission circuit 44.

The digital image signal stored in the image data memory 43 is appropriately transmitted to the cassette control section 30. A storage section 31 is connected to the cassette control section 30. The cassette control section 30 stores the transmitted digital image signal as image data in the storage section 31.

Here, the flow of an electric signal in radiography, the flow of an electric signal in the dark reading, and the like are described.

In radiography by which a subject is radiographed, when a radiation passing through the subject is incident on the scintillator layer, light is delivered to the sensor panel section 24 from the scintillator layer. The characteristics of the photoelectric conversion elements 23 are changed according to the amount of the light received thereat.

When radiography is ended, radiographed image data is read as electric signals from the radiation image detector 1. At the time, a reading voltage is applied to the gate electrode of each of TFTs 41 from a scan line Ll, so that the gate of each of the TFTs 41 opens. Electric signals are read as signal values from the respective photoelectric conversion elements 23 via the respective TFTs 41 to the respective signal lines Lr. The signal values are, for example, amplified by the respective amplifier circuits 37, and then transmitted to the respective A/D converters 42 from the respective analog multiplexers 39 successively. The signals converted into digital signals are stored in the image data memory 43 on a photoelectric conversion element 23-by-photoelectric conversion element 23 basis (namely, on a pixel-by-pixel basis). The signals stored in the image data memory 43 are appropriately transmitted to the cassette control section 30 via the transmission circuit 44, and stored in the storage section 31 as radiographed image data.

Electric signals are read from all the photoelectric conversion elements 23 of the sensor panel section 24 by successively scanning the scan lines Ll, each of which applies a reading voltage to TFTs 41, and by performing the reading processing described above on each of the scan lines Ll. As a result, radiographed image data obtained by detecting a signal from each of the photoelectric conversion elements 23, amplifying the signal, and the like, is stored in the storage section 31 as data on a photoelectric conversion element 23-by-photoelectric conversion element 23 basis (namely, on a pixel-by-pixel basis) in one radiography.

On the other hand, in the dark reading, all the photoelectric conversion elements 23 of the FPD cassette 2 are once reset so as to emit charges. Then, the gate of each of the TFTs 41 closes, and the FPD cassette 2 is left without being irradiated.

After a prescribed time elapses, a reading voltage is applied to the gate electrode of each of TFTs 41 from a scan line Ll, so that the gate of each of the TFTs 41 opens. Charges accumulated in the respective photoelectric conversion elements 23 are read therefrom to the respective signal lines Lr. In a similar way to the way of radiography, the charges are amplified by the respective amplifier circuits 37, the like, and then transmitted to the respective A/D converters 42 via the respective analog multiplexers 39 successively. The signals converted into digital signals are stored in the image data memory 43 on a photoelectric conversion element 23-by-photoelectric conversion element 23 basis (namely, on a pixel-by-pixel basis). Output values (dark image data) obtained by, for example, amplifying the respective charges outputted from the respective photoelectric conversion elements 23 without being irradiated are referred to as "dark reading values" hereinafter. The dark reading values stored in the image data memory 43 are appropriately transmitted to the cassette control section 30 via the transmission circuit 44, and stored in the storage section 31 as dark reading values of the respective photoelectric conversion elements 23.

Electric signals are read from all the photoelectric conversion elements 23 of the sensor panel section 24 by successively scanning the scan lines Ll, each of which applies a reading voltage to TFTs 41, and by performing the reading processing described above on each of the scan lines Ll. As a result, dark reading values are obtained with regard to all the photoelectric conversion elements 23, and the obtained dark reading values are stored in the storage section 31 as data on a photoelectric conversion element 23-by-photoelectric conversion element 23 basis (namely, on a pixel-by-pixel basis).

In the embodiment of the present invention, the dark reading is performed multiple times at the FPD cassette 2 right before each time radiography is performed, namely, when an irradiation instruction signal is transmitted to the radiation generator 4 from the operation device 7. A dark reading value is outputted from each photoelectric conversion element 23 each time the dark reading is performed. The cassette control section 30 calculates the average value of dark reading values (output values) obtained by performing the dark reading multiple times. Calculation of the average value is performed with regard to all the photoelectric conversion elements 23. Average values obtained thereby are stored in the storage section 31 as offset correction values.

A standard number of times the dark reading is performed in order to generate the offset correction values is not limited. For example, the offset correction values may be generated by performing the dark reading one time. In this case, calculation of the average value of dark reading values with regard to all photoelectric conversion elements 23 is unnecessary, and dark reading values obtained by the one-time dark reading are used as the offset correction values.

More times the dark reading is performed, the less influenced by superposition of noise and more stable offset correction values can be calculated. Instead, it takes longer time to obtain the offset correction values, and the battery 28 is consumed. In the embodiment of the present invention, the dark reading is performed five times right before each time radiography is performed so as to calculate the offset correction values, which is a case to be described as an example in the following.

In the embodiment of the present invention, the battery 28 described below (shown in FIG. 4) is being charged even during the dark reading. The cassette control section 30 controls the sensor panel section 24 and the reading section 45 to perform the dark reading one time more than the prescribed standard number of times (five times in the embodiment) when detecting that a cable or the like is connected to the connector section 26 during the dark reading. How many times more the dark reading is performed than the prescribed standard number of times is not limited thereto, and the dark reading may be performed two or more times in addition to the prescribed standard number of times.

When the cable 49 is connected to the connector section 26 during the dark reading, and an ON/OFF switch SW (shown in FIG. 4) is turned to ON, a large amount of power is supplied from the external power source PW to the battery 28 at the moment. Accordingly, the most noise may be superposed on dark reading values obtained in the dark reading which is being performed at the moment the ON/OFF switch SW is turned to ON. Therefore, it is preferable that the cassette control section 30 discard the dark reading values obtained in the dark reading which is being performed at the moment the ON/OFF switch SW is turned to ON, perform the dark reading one time more than the standard number of times excluding the time when the discarded dark reading values are obtained, and use the average values of dark reading values obtained thereby as offset correction values.

FIG. 4 is a main-part block diagram showing a functional structure of the FPD cassette 2, and a power supply circuit which charges the battery 28 of the FPD cassette 2.

As shown in FIG. 4, the FPD cassette 2 includes the cassette control section 30, the storage section 31, the scan driving circuit 32, the signal reading section 33 including the signal reading circuit 40, a timing section 34, a communication section 35, the bias power source 36, the external power supply terminal 27, and the battery 28.

The cassette control section 30 is a computer including a CPU (Central Processing Unit), a ROM (Read Only Memory), and a RAM (Random Access Memory), which are not shown. The cassette control section 30 is an arithmetic section which generates image data and calculates offset correction values.

The ROM stores programs for performing various processing at the FPD cassette 2, the processing such as radiographed image data generation processing and offset correction value generation processing; various control programs; parameters; and the like.

The cassette control section 30 reads a prescribed program from the ROM, the program which is stored therein, expands the program in a work area of the RAM, and performs processing according to the program.

In the embodiment of the present invention, an image data generation section is composed of the reading section 45 including the cassette control section 30, which is the arithmetic section, and the sensor panel section 24.

The storage section 31 is composed of a HDD (Hard Disk Drive), a flash memory, or the like, and stores radiographed image data (image data based on a radiation passing through a subject) generated by the reading section 45 (shown in FIG. 4), dark reading values (image data obtained without irradiation), offset correction values, and the like.

The storage section 31 may be a built-in memory or a removable memory such as a memory card. The capacity of the storage section 31 is not limited. However, it is preferable that the storage section 31 have the capacity which can store image data of a plurality of images. Having such a storage section makes it possible to successively irradiate a subject, and record and accumulate image data each time the subject is irradiated. As a result, seriography and video shooting become available.

The timing section 34 measures an elapsed time which is a time elapsed since an irradiation instruction signal is transmitted from the operation device 7. The timing section 34 outputs information to the cassette control section 30, the information on a time elapsed since an irradiation instruction signal is transmitted. The timing section 34 may function in the cassette control section 30 as software.

The communication section 35 is a communication section which is connected to the antenna device 46, and transmits and receives various signals to/from an external device such as the console 5 according to control of the cassette control section 30. The communication section 35 communicates with an external device such as the console 5 via the wireless access point 6 by a wireless method.

In the embodiment of the present invention, the communication section 35 transmits image data (radiographed image data or data obtained by the dark reading) to the console 5, which is an external device, based on an image signal read by the reading section 45, and also receives radiography order information from the console 5 or the like.

The FPD cassette 2 includes the battery 28 as an internal power supply section to supply power to each section of the FPD cassette 2.

As the battery 28, a nickel-cadmium battery, a nickel-hydrogen battery, a lithium-ion battery, a small sealed storage lead-acid battery, a lead-acid storage battery, an electric double layer capacitor, or the like, which can be charged, can be used.

The external power supply terminal 27 is connected to the connector section 26. The cable 49 which is connected to the external power source PW is connected to the connector section 26, so that the cable 49 is connected to the external power supply terminal 27 via the connector section 26. When the cable 49 is connected to the connector section 26, the external power supply terminal 27 receives power supplied from the external power source PW, and can supply the power to the battery 28 accordingly.

As shown in FIG. 4, on a power supply circuit C between the external power supply terminal 27 and the battery 28, the ON/OFF switch SW which switches ON and OFF of power supply, the power supplied from the external power source PW to the battery 28, is provided. Power supply from the external power supply terminal 27 to the battery 28 can be controlled by the cassette control section 30 controlling the ON/OFF switch SW. In the embodiment of the present invention, the cassette control section 30 functions as a power supply control section to control power supply from the external power source PW to the battery 28.

Here, the control of power supply from the external power source PW to the battery 28 by the cassette control section 30 is described.

In the embodiment of the present invention, when the cable 49 is connected to the connector section 26, the cassette control section 30 detects that the cable 49 is connected to the connector section 26. When the cassette control section 30 detects that the external power supply terminal 27 receives power from the external power source PW, the cassette control section 30 judges an operating state of each section, and controls power supply to the battery 28, the power received from the external power source PW via the external power supply terminal 27, in accordance with the operating state of each section.

Namely, for example, when the cable 49 is connected to the connector section 26, and power supply from the external power source PW becomes available accordingly, the cassette control section 30 judges whether the reading processing of radiographed image data is being performed at the sensor panel section 24 and/or the reading section 45 or not, and outputs a control signal S1 to switch the ON/OFF switch SW to OFF while the reading processing is being performed. As a result, the power supply from the external power supply terminal 27 to the battery 28 stops, namely, the power supply is controlled not to charge the battery 28.

More specifically, as described above, the radiation generator 4 performs irradiation for a prescribed duration after a prescribed time elapses since an irradiation instruction signal is transmitted, and the cassette control section 30 judges whether irradiation is performed from an elapsed time which is outputted from the timing section 34. Then, the cassette control section 30 controls the ON/OFF switch SW to be turned to OFF during a time which irradiation is performed by the radiation generator 4 and during a prescribed time which is necessary for reading image signals after irradiation.

How much time after an irradiation instruction signal being transmitted, irradiation is actually performed; how much time irradiation is performed; and how much time is necessary as a prescribed time for reading image signals since the end of irradiation are predetermined according to a region to be radiographed and the like. The cassette control section 30 judges these times mentioned above based on radiography order information and the like each time radiography is performed, and controls the ON/OFF switch SW. The detection section to detect a radiation may be provided with the FPD cassette 2, and the start and the end of irradiation may be judged based on a result of the detection performed by the detection section.

The cassette control section 30 outputs a control signal S1 to turn the ON/OFF switch SW to ON when judging that the dark reading is being performed at the sensor panel section 24 and the reading section 45. Consequently, power is supplied from the external power supply terminal 27 to the battery 28 so as to charge the battery 28.

In this case, much noise is generated at the moment a large amount of power is supplied from the external power source PW to the battery 28 by turning the ON/OFF switch SW to ON. Hence, as described above, it is preferable to discard the dark reading values which are obtained in the dark reading being performed at the moment the ON/OFF switch SW is turned to ON.

The cassette control section 30 judges an operating state of the communication section 35. When the communication section 35 is transmitting image data (radiographed image data or data obtained by dark reading), the cassette control section 30 outputs a control signal S1 to turn the ON/OFF switch SW to OFF. Consequently, power supply from the external power supply terminal 27 to the battery 28 stops, namely, power supply is controlled so as not to charge the battery 28.

When the remaining charged amount of the battery 28 becomes insufficient while image data is being transmitted, the cassette control section 30 once cancels transmitting the image data, and outputs a control signal S1 to turn the ON/OFF switch SW to ON. Consequently, power is supplied from the external power supply terminal 27 to the battery 28 so as to charge the battery 28. After the battery 38 is charged, the image data stored in the storage section 31 is re-transmitted to the console 5.

Figure 5:
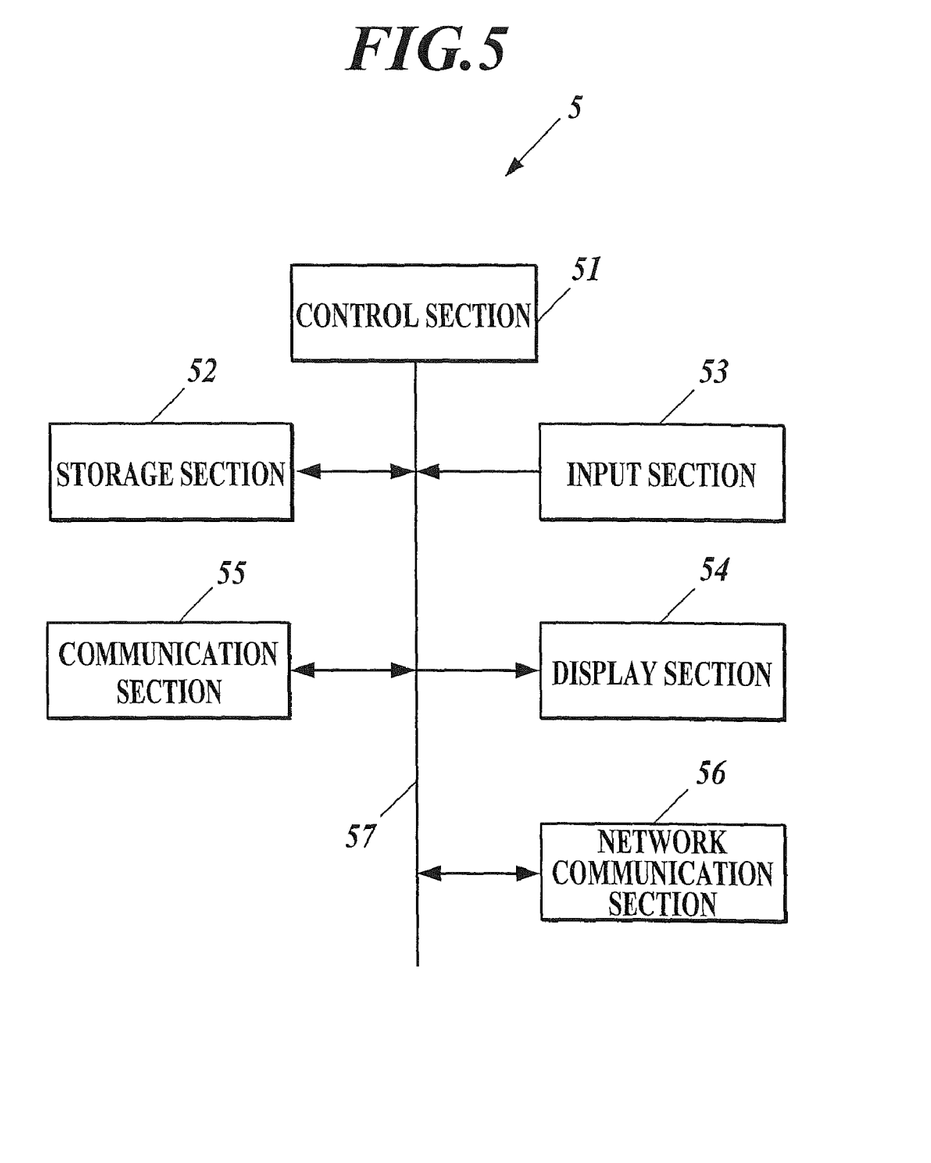
FIG. 5 is a main-part block diagram showing a functional structure of a console applied to the radiography system shown in FIG. 1.

The console 5 includes, as shown in FIG. 5, a control section 51 composed of a CPU (Central Processing Unit) and the like, a storage section 52, an input section 53, a display section 54, a communication section 55, and a network communication section 56. The sections of the console 5 are connected to each other by a bus 57.

The storage section 52 includes a ROM (Read Only Memory) and a RAM (Random Access Memory).

The ROM is composed of, for example, a HDD (Hard Disk Drive), a nonvolatile semiconductor memory, or the like. The ROM stores various programs including a program for image processing such as gradation processing or frequency processing based on automatic region recognition for detecting an affected region, image processing parameters (a look-up table which defines a gradation curve used for gradation processing, an enhancement degree for frequency processing, and the like) for adjusting image data of a taken image to be a suitable quality for diagnosis, and the like.

The RAM forms a work area to temporarily store each program which is read from the ROM and is executable by the control section 51, input and/or output data, parameters, and the like in each processing performed and controlled by the control section 51.

In the embodiment of the present invention, the storage section 52 stores patient information, radiography order information, and the like. In addition, the storage section 52 temporarily stores radiographed image data transmitted from the FPD cassette 2, information attached thereto, and the like.

The control section 51 is a control section of the console 5 to read a program from various programs stored in the ROM, the programs such as a system program and a processing program stored in the ROM, expand the read program in the RAM, and perform processing in accordance with the expanded program.

The control section 51 is a display control section to control the display section 54 so as to display an image based on radiographed image data transmitted from the FPD cassette 2.

In addition to obtaining patient information on a patient who provides a subject and radiography order information, the control section 51 functions as a correlation section to correlate the obtained patient information and radiography order information with image data generated at the FPD cassette 2 and transmitted to the console 5. The radiography order information and the like may be inputted from the input section 53 and stored in the storage section 52 or the like, or may be obtained from a HIS/RIS 8 or the like where subject information (radiography order information) is registered in advance.

The control section 51 performs the offset correction on radiographed image data transmitted from the FPD cassette 2 by using offset correction values.

The control section 51 also extracts a gain correction value for the FPD cassette used for radiography from among gain correction values stored in the HIS/RIS or the like based on a cassette ID, each of the gain correction values corresponding to each FPD cassette, and performs the gain correction by using the extracted gain correction value.

The control section 51 performs, according to a radiographed region, image processing such as gradation processing and frequency processing on radiographed image data after the offset correction and the gain correction are performed thereon, and generates final image data for diagnosis.

The input section 53 includes a keyboard having character input keys, number input keys, various function keys, and the like, and a pointing device such as a mouse. The input section 53 outputs a depression signal of a key which is depressed on the keyboard and an operation signal of the mouse, as input signals to the control section 51.

The display section 54 includes a monitor such as a CRT (Cathode Ray Tube) or a LCD (Liquid Crystal Display), and displays each of various screens in accordance with an instruction of a display signal inputted from the control section 51.

The communication section 55 transmits and receives information to/from the FPD cassette 2 and the like via the wireless access point 6 by a wireless method.

The network communication section 56 includes a network interface, and transmits and receives data to/from an external device connected to a network N via a switching hub.

In the embodiment of the present invention, the HIS/RIS 8, a PACS server 9, an imager 10, and the like are the external devices connected to the network communication section 56 of the console 5 via the network N. However, the external devices connected to the network N are not limited thereto.

The HIS/RIS 8 provides radiography order information on radiography a subject to the console 5. The radiography order information includes patient information on a patient who provides a subject for examinations, the patient information including the name of the patient, and information on a radiography booking including a region to be radiographed, a radiography method, and a type of the Bucky device 3 (the Bucky device 3a for radiography in the decubitus position, the Bucky device 3b for radiography in the standing position, or the like) used for radiography. The radiography order information is not limited thereto, and may include information other than the information mentioned above or may be some of the information mentioned above.

In the embodiment of the present invention, the HIS/RIS 8 is a storage section to store gain correction values and the like, which are predetermined for the FPD cassettes 2, respectively. The gain correction values are correlated with cassette IDs of the respective FPD cassettes 2, respectively, therein. The storage section to store offset correction values and gain correction values is not limited to the HIS/RIS 8.

The PACS server 9 stores final image data for diagnosis outputted from the console 5.

The imager 10 records radiation images on an image recording medium such as a film based on the final image data outputted from the console 5, and outputs the radiation images.

Next, operation of the FPD cassette 2 in the embodiment of the present invention is described.

When the cable 49 is connected to the connector section 26, the cassette control section 30 judges whether or not the reading processing of radiographed image data is being performed at the sensor panel section 24 and the reading section 45 based on information outputted from the timing section 34, radiography order information, and the like, and also judges whether or not image data is being transmitted from the communication section 35 to the console 5.

When the reading processing of the radiographed image data is being performed, or image data (radiographed image data or data obtained by dark reading) is being transmitted, the ON/OFF switch SW is turned to OFF so as not to charge the battery 28. After the reading processing of the radiographed image data ends, namely, after irradiation ends and a prescribed time necessary for the reading processing elapses, or after transmission of the image data ends, the ON/OFF switch SW is turned to ON, and power is supplied to the battery 28 from the external power source PW accordingly so as to charge the battery 28.

When the remaining charged amount of the battery 28 becomes insufficient while the image data is being transmitted, transmission processing of the image data is cancelled. The image data stored in the storage section 31 is re-transmitted to the console 5 after the battery 28 is charged. When completing reception of the image data, the control section 51 of the console 5 transmits a signal notifying that the reception of the image data is completed to the FPD cassette 2. When receiving the signal notifying that the reception of the image data is completed from the control section 51 of the console 5, the cassette control section 30 deletes the image data stored in the storage section 31.

On the other hand, when the reading processing of the radiographed image data is not being performed and the image data is not being transmitted, the ON/OFF switch SW is turned to ON, and power is supplied from the external power source PW to the battery 28 accordingly so as to charge the battery 28. However, when the dark reading is being performed at the time, the cassette control section 30 controls the sensor panel section 24 and the reading section 45 to perform the dark reading one time more than the prescribed number of times.

As described above, when the cable 49 is connected to the connector section 26 during the dark reading, and a large amount of power is supplied from the external power source PW, it is preferable that the cassette control section 30 discard dark reading values obtained in the dark reading performed at the moment the ON/OFF switch SW is turned to ON, and perform the dark reading one time more than the standard number of times excluding the time when the discarded dark reading values are obtained, and uses the average values of dark reading values obtained thereby as offset correction values.

As described above, according to the embodiment of the present invention, the battery 28 is not charged during the reading processing of radiographed image data. In addition, although the battery 28 is charged during the dark reading, the dark reading is performed one time more than the prescribed standard number of times.

When power is supplied from the external power source PW to the battery 28 so as to charge the battery 28, a large amount of power is supplied from the external power source PW during charging. Hence, if the reading processing of signals is performed at the same time, noise is superposed on the signals. However, in the embodiment of the present invention, superposition of noise on radiographed image data can be prevented, so that high quality images can be obtained. Furthermore, when the battery 28 is charged during the dark reading, noise is superposed on dark reading values. However, influence of the noise thereon can be reduced by increasing the number of times the dark reading is performed and averaging dark reading values obtained thereby. As a result, appropriate offset correction values can be calculated while charging is being performed.

If the battery 28 is charged while image data is being transmitted from the communication section 35 of the FPD cassette 2 to the console 5, noise is superposed on signals thereof. In the embodiment of the present invention, the battery 28 is not charged while image data is being transmitted from the communication section 35 of the FPD cassette 2 to the battery 28. As a result, it can be prevented that noise resulted from power supplied from the external power source PW influences the image data in transmission.

In the embodiment of the present invention, the battery 28 is not charged while the reading processing of radiographed image data is being performed or image data is being transmitted from the communication section 35 to the console 5. Furthermore, the battery 28 is charged while the dark reading is being performed, but the dark reading is performed one time more than the prescribed standard number of times. However, how to control power supply from the external power source PW to the battery 28 is not limited thereto.

For example, when the reading processing of radiographed image data is being performed or the dark reading is being performed, the cassette control section 30 may control power supply to the battery 28 so as to limit the amount of power received from the external power source PW to a prescribed amount of power, and supply the prescribed amount of power to the battery 28, by judging that the image data generation section is in operation, and when the reading processing of radiographed image data is not being performed and the dark reading is not being performed, the cassette control section 30 may control power supply to the battery 28 so as not to limit the amount of power received from the external power source PW, and supply the amount of power to the battery 28, by judging that the image data generation section is not in operation.

Similarly, when image data is being transmitted from the communication section 35 to the console 5, the cassette control section 30 may control power supply to the battery 28 so as to limit the amount of power received from the external power source PW to a prescribed amount of power, and supply the prescribed amount of power to the battery 28, by judging that the image data generation section is in operation, and when image data is not being transmitted from the communication section 35 to the console 5, the cassette control section 30 may control power supply to the battery 28 so as not to limit the amount of power received from the external power source PW and supply the amount of power to the battery 28, by judging that the image data generation section is not in operation.

The prescribed amount of power is the amount of power necessary for operating each section plus some extra. When charging is performed by limiting the amount of power, it requires longer time to complete charging, but can prevent noise from being generated. As a result, the battery 28 can be charged without noise influencing image data.

When, by judging that the image data generation section is in operation, the cassette control section 30 does not charge the battery 28, or limits the amount of power received from the external power source PW to a prescribed amount of power so as to supply the prescribed amount of power to the battery 28, what makes the cassette control section 30 judge that the image data generation section is in operation can be predetermined.

For example, the image data generation section may be judged to be in operation based on that the reading processing of radiographed image data is being performed (namely, radiographed image data is being generated) or the dark reading is being performed.

Moreover, the image data generation section may be judged to be in operation based on that a series of processing for one radiography is being performed by the image data generation section. In this case, for example, when an irradiation instruction signal is transmitted and the dark reading is performed, and radiographed image data is generated by irradiation thereafter, a series of processing for one radiography is regarded as being ended. A series of processing for one radiography may be regarded as being ended when an irradiation instruction signal is transmitted and radiographed image data is generated by irradiation, and the dark reading is performed thereafter.

While radiography is being performed according to radiography order information on a same patient, the cassette control section 30 may judge that the image data generation section is in operation.

As described above, the possibility that noise is superposed on signals can be excluded for certain by judging that the image data generation section is in operation based on that a series of processing for one radiography is being performed by the image data generation section or that radiography is being performed according to radiography order information on a same patient.

When the gain correction is performed at the FPD cassette 2, the cassette control section 30 may judge that the image data generation section is in operation based on that the gain correction is being performed (namely, gain calibration is being performed).

In the embodiment of the present invention, the FPD cassette 2 includes the timing section, and the timing section 34 measures a time elapsed since an irradiation instruction signal is transmitted, and the ON/OFF switch SW is controlled by judging whether the reading processing is being performed or not. However, how to judge whether the reading processing is being performed or not is not limited thereto. For example, the console 5 may transmit an elapsed time to the FPD cassette 2, the elapsed time, which is a time elapsed since an irradiation instruction signal is transmitted, and the cassette control section 30 may judge whether the reading processing is being performed or not based thereon.

In the embodiment of the present invention, when offset correction values are generated at the FPD cassette 2, the offset correction values are transmitted to the console 5 with image data so that the offset correction is performed at the console 5. However, when offset correction values are generated at the FPD cassette 2, the offset correction may be performed at the cassette control section 30 of the FPD cassette 2 by using the offset correction values, and image data may be transmitted to the console 5 after the offset correction is performed thereon.

In the embodiment of the present invention, when the dark reading is performed at the FPD cassette 2, the cassette control section 30 functions as an offset correction value generation section to calculate offset correction values by calculating the average values of dark reading values, or the like. However, offset correction values are not limited to being generated at the cassette control section 30. For example, when the dark reading is performed at the FPD cassette 2, dark reading values obtained by performing the dark reading (data in which dark reading values for five-times dark reading obtained by performing the dark reading five times are added up, for example) may be transmitted to the console 5 with radiographed image data, and the control section 51 of the console 5 may calculate offset correction values from the dark reading values (calculate the average values of the dark reading values for five-times dark reading, for example) and perform the offset correction.

In the embodiment of the present invention, the operation device 7 is provided in the preparation room R2, and the console 5 to control the radiography system 1 as a whole is provided separately therefrom. However, the console 5 may be provided for each preparation room R2 instead of the operation device 7. In this case, in addition to controlling the radiography system 1 as a whole, the console 5 controls the radiation generator 4, operates the Bucky device 3, and the like, as needed.

In the embodiment of the present invention, radiography order information is read from the storage section 52 by the control section 51 of the console 5, the storage section 52 where the radiography order information is stored in advance, or obtained from the HIS/RIS 8 or the like via the network N, the HIS/RIS 8 where the radiography order information is registered in advance. However, the radiography order information is not always needed to be generated before radiography. Radiography order information may be generated after radiography so as to be correlated with obtained image data.

In the embodiment of the present invention, the cable 49 is directly connected to the connector section 26. However, how to connect the cable 49 to the connector section 26 is not limited thereto. For example, when the FPD cassette 2 is placed on a cradle or the like, or loaded into the Bucky device 3, the cable 49 connected to the external power source PW or the like may be indirectly connected to the connector section 26 of the FPD cassette 2 via the cradle or the Bucky device 3.

It is needless to mention that the present invention is not limited to the embodiment and can be appropriately modified.

INDUSTRIAL APPLICABILITY

The present invention is industrially applicable to a radiation image detector to obtain radiation images for diagnosis in the medical field.

EXPLANATION OF REFERENCES 1 radiography system
2 FPD cassette (radiation image detector)
5 console
7 operation device
22 power source switch
24 antenna device
27 external power supply terminal
28 battery
30 cassette control section
35 communication section
51 control section
55 communication section
N network
R1 radiography room
R2 preparation room

The invention claimed is:

1. A radiation image detector comprising:
an image data generation section including,
    a detection section in which a plurality of radiation detection elements are two-dimensionally arranged so as to be capable of extracting an electric signal of each pixel,
    a reading section to read the electric signal obtained by the detection section, and
    an arithmetic section;
a communication section to transmit image data generated by the image data generation section to an outside of the radiation image detector;
an internal power supply section, which is capable of being charged, to supply power to each of the sections including the detection section and the reading section;
an external power supply terminal to receive power from an external power source so as to allow the internal power supply section to be charged; and
a power supply control section to control supply of the power to the internal power supply section, the power being received from the external power source via the external power supply terminal, wherein
when the power supply control section detects that the external power supply terminal receives power from the external power source, the power supply control section judges an operating state of each of the sections, and controls supply of the power to the internal power supply section according to the operating state of each of the sections, the power being received from the external power source via the external power supply terminal.

2. The radiation image detector according to claim 1, wherein when the image data generation section generates radiographed image data, the power supply control section controls power supply not to supply the power to the internal power supply section, the power being received from the external power source.

3. The radiation image detector according to claim 1, wherein when the communication section transmits image data to the outside, the power supply control section controls power supply not to supply the power to the internal power supply section, the power being received from the external power source.

4. The radiation image detector according to claim 1, wherein
when dark reading to read an output value of each of the radiation detection elements is performed by the image data generation section in a state where irradiation is not performed, the power supply control section controls power supply to supply the power to the internal power supply section, the power being received from the external power source, and
when the power received from the external power source is supplied to the internal power supply section, the image data generation section performs the dark reading more than a prescribed standard number of times.

5. The radiation image detector according to claim 1, wherein the power supply control section controls power supply to the internal power supply section, by which the power supply control section limits an amount of the power received from the external power source to a prescribed amount of the power and supplies the prescribed amount of the power to the internal power supply section when the image data generation section is in operation, and does not limit the amount of the power received from the external power source and supplies the amount of the power to the internal power supply section when the image data generation section is not in operation.

6. The radiation image detector according to claim 5, wherein when the reading section reads the electric signal obtained by the detection section, the power supply control section judges that the image data generation section is in operation.

7. The radiation image detector according to claim 5, wherein while the image data generation section performs a series of processing for one radiography, the power supply control section judges that the image data generation section is in operation.

8. The radiation image detector according to claim 5, wherein
the communication section receives radiography order information from the outside, and
while radiography is performed according to the radiography order information on a same patient, the power supply control section judges that the image data generation section is in operation.

9. The radiation image detector according to claim 1, wherein the power supply control section controls power supply to the internal power supply section, by which the power supply control section limits an amount of the power received from the external power source to a prescribed amount of the power and supplies the prescribed amount of the power to the internal power supply section when the communication section is in operation, and does not limit the amount of the power received from the external power source and supplies the amount of the power to the internal power supply section when the communication section is not in operation.

* * * * *